United States Patent
Kido et al.

(10) Patent No.: US 10,441,742 B2
(45) Date of Patent: Oct. 15, 2019

(54) LIGHT EMISSION CONTROL DEVICE, ELECTRONIC DEVICE, AND CONTROL METHOD

(71) Applicants: Panasonic Corporation, Osaka (JP); Nintendo Co., Ltd., Kyoto (JP)

(72) Inventors: Hiroshi Kido, Osaka (JP); Shigeru Ido, Osaka (JP); Hisao Kataoka, Osaka (JP); Naohiro Toda, Chiba (JP); Kazuhiro Hatta, Osaka (JP); Sadayoshi Hattori, Kyoto (JP)

(73) Assignees: Panasonic Corporation, Osaka (JP); Nintendo Co., Ltd., Kyoto (JP)

( * ) Notice: Subject to any disclaimer, the term of this patent is extended or adjusted under 35 U.S.C. 154(b) by 0 days.

(21) Appl. No.: 15/904,326

(22) Filed: Feb. 24, 2018

(65) Prior Publication Data

US 2018/0250492 A1    Sep. 6, 2018

(30) Foreign Application Priority Data

Mar. 1, 2017  (JP) .................... 2017-038709

(51) Int. Cl.
| | |
|---|---|
| *H05B 33/08* | (2006.01) |
| *H05B 37/02* | (2006.01) |
| *A61M 21/00* | (2006.01) |
| *A61B 5/00* | (2006.01) |
| *G04G 13/02* | (2006.01) |
| *G04G 11/00* | (2006.01) |
| *A61N 5/06* | (2006.01) |

(52) U.S. Cl.
CPC ........... *A61M 21/00* (2013.01); *A61B 5/4812* (2013.01); *G04G 11/00* (2013.01); *G04G 13/02* (2013.01);
(Continued)

(58) Field of Classification Search
CPC ............ F21Y 2115/10; H05B 37/0272; H05B 37/0281; H05B 33/0845; H05B 33/086; H05B 33/0872; H05B 37/0218; H05B 37/0227; H05B 33/0815; H05B 33/0854; H05B 33/0857; H05B 33/0863; H05B 33/0866; H05B 37/0245; A61M 21/00; A61M 2021/0044; A61M 2021/0083; A61N 2005/0663; G04G 11/00
See application file for complete search history.

(56) References Cited

U.S. PATENT DOCUMENTS 9,137,867 B2 *  9/2015  Kamii ................. H05B 33/086
9,362,364 B2 *  6/2016  Park .................... H01L 21/8258
(Continued)

FOREIGN PATENT DOCUMENTS

JP    2011-92271 A    5/2011

OTHER PUBLICATIONS

Extended European Search Report for corresponding EP patent application No. 18158805.4, dated Jun. 21, 2018.

*Primary Examiner* — Vibol Tan
(74) *Attorney, Agent, or Firm* — Renner, Otto, Boisselle & Sklar, LLP

(57) ABSTRACT

A light emission control device includes a light emission controller which controls a light emitter and performs normal control and wake-up control, the normal control being control for causing the light emitter to emit light having a color temperature and luminance according to an instruction of a user, the wake-up control being control for causing the light emitter to emit light at increasing luminance over time to wake up the user who is sleeping. The maximum luminance of light emitted by the light emitter in the wake-up control is greater than the maximum luminance of light emitted by the light emitter in the normal control.

14 Claims, 16 Drawing Sheets

(52) U.S. Cl.
CPC ....... *H05B 33/086* (2013.01); *H05B 33/0818* (2013.01); *H05B 37/0281* (2013.01); *A61M 2021/0027* (2013.01); *A61M 2021/0044* (2013.01); *A61M 2021/0083* (2013.01); *A61M 2209/01* (2013.01); *A61M 2230/04* (2013.01); *A61M 2230/10* (2013.01); *A61M 2230/14* (2013.01); *A61M 2230/60* (2013.01); *A61M 2230/63* (2013.01); *A61N 2005/0663* (2013.01); *H05B 37/0227* (2013.01); *Y02B 20/42* (2013.01)

(56) References Cited

U.S. PATENT DOCUMENTS

| | | | |
|---|---|---|---|
| 9,636,520 B2* | 5/2017 | Pedersen | A61N 5/0618 |
| 2007/0118026 A1* | 5/2007 | Kameyama | A61B 5/0261 |
| | | | 600/300 |
| 2008/0224635 A1* | 9/2008 | Hayes | H05B 35/00 |
| | | | 315/297 |
| 2012/0032616 A1* | 2/2012 | Toda | A61M 21/00 |
| | | | 315/360 |
| 2013/0038244 A1* | 2/2013 | Kamii | H05B 33/0818 |
| | | | 315/297 |
| 2015/0102749 A1* | 4/2015 | Soler | A61N 5/0618 |
| | | | 315/307 |
| 2015/0305126 A1* | 10/2015 | Maeda | H05B 37/0281 |
| | | | 315/134 |
| 2016/0366746 A1* | 12/2016 | van de Ven | F21V 29/74 |
| 2017/0031324 A1* | 2/2017 | Toda | G04G 11/00 |
| 2017/0196058 A1* | 7/2017 | Morneau | H05B 33/0815 |

\* cited by examiner (a) SLEEP STATE (b) LUMINANCE (a) SLEEP STATE (b) LUMINANCE (a) SLEEP STATE (b) LUMINANCE

LIGHT EMISSION CONTROL DEVICE, ELECTRONIC DEVICE, AND CONTROL METHOD

CROSS REFERENCE TO RELATED APPLICATION

This application claims the benefit of priority of Japanese Patent Application Number 2017-038709 filed on Mar. 1, 2017, the entire content of which is hereby incorporated by reference.

BACKGROUND

1. Technical Field

The present disclosure relates to a light emission control device capable of performing light emission control (wake-up control) for waking up a sleeping user, and an electronic device including the light emission control device.

2. Description of the Related Art

Conventionally, illumination apparatuses (luminaires) including light-emitting elements such as light-emitting diodes (LEDs) have been used for various purposes. For example, Patent Literature (PTL) 1 (Japanese Unexamined Patent Application Publication No. 2011-92271) discloses an illumination apparatus which assists a sleeping user to wake up by emitting light onto the sleeping user.

SUMMARY

An illumination apparatus for assisting a person to wake up as described above is required to have a function of effectively waking up a user.

The present disclosure provides a light emission control device and an electronic device which are capable of effectively waking up a user.

A light emission control device according to one aspect of the present disclosure includes a light emission controller which controls a light emitter and performs normal control and wake-up control, the normal control being control for causing the light emitter to emit light having a color temperature and luminance according to an instruction of a user, the wake-up control being control for causing the light emitter to emit light at increasing luminance over time to wake up the user who is sleeping. The maximum luminance of light emitted by the light emitter in the wake-up control is greater than the maximum luminance of light emitted by the light emitter in the normal control.

An electronic device according to one aspect of the present disclosure includes the light emission control device and a case which houses the light emission control device.

A light emission control device and an electronic device of the present disclosure make it possible to stabilize luminance and a color temperature of a light emitter in normal control and effectively wake up a user by wake-up control.

BRIEF DESCRIPTION OF DRAWINGS

The figures depict one or more implementations in accordance with the present teaching, by way of examples only, not by way of limitations. In the figures, like reference numerals refer to the same or similar elements.

DETAILED DESCRIPTION OF THE EMBODIMENTS

Hereinafter, embodiments will be described with reference to the Drawings. It should be noted that the embodiments described below each represent a generic or specific example. The numerical values, shapes, materials, structural components, the arrangement and connection of the structural components, steps, the order of the steps, etc. shown in the following embodiments are mere examples, and are not intended to limit the scope of the present disclosure. Furthermore, among the structural components in the following embodiments, structural components not recited in any one of the independent claims which indicate the broadest concepts of the present disclosure are described as optional structural components.

It should be noted that the figures are schematic diagrams and are not necessarily precise illustrations. Furthermore, in the figures, substantially identical components are assigned the same reference signs, and overlapping description may be omitted or simplified.

(Embodiment 1)
[Entire Configuration]

Figure 1:
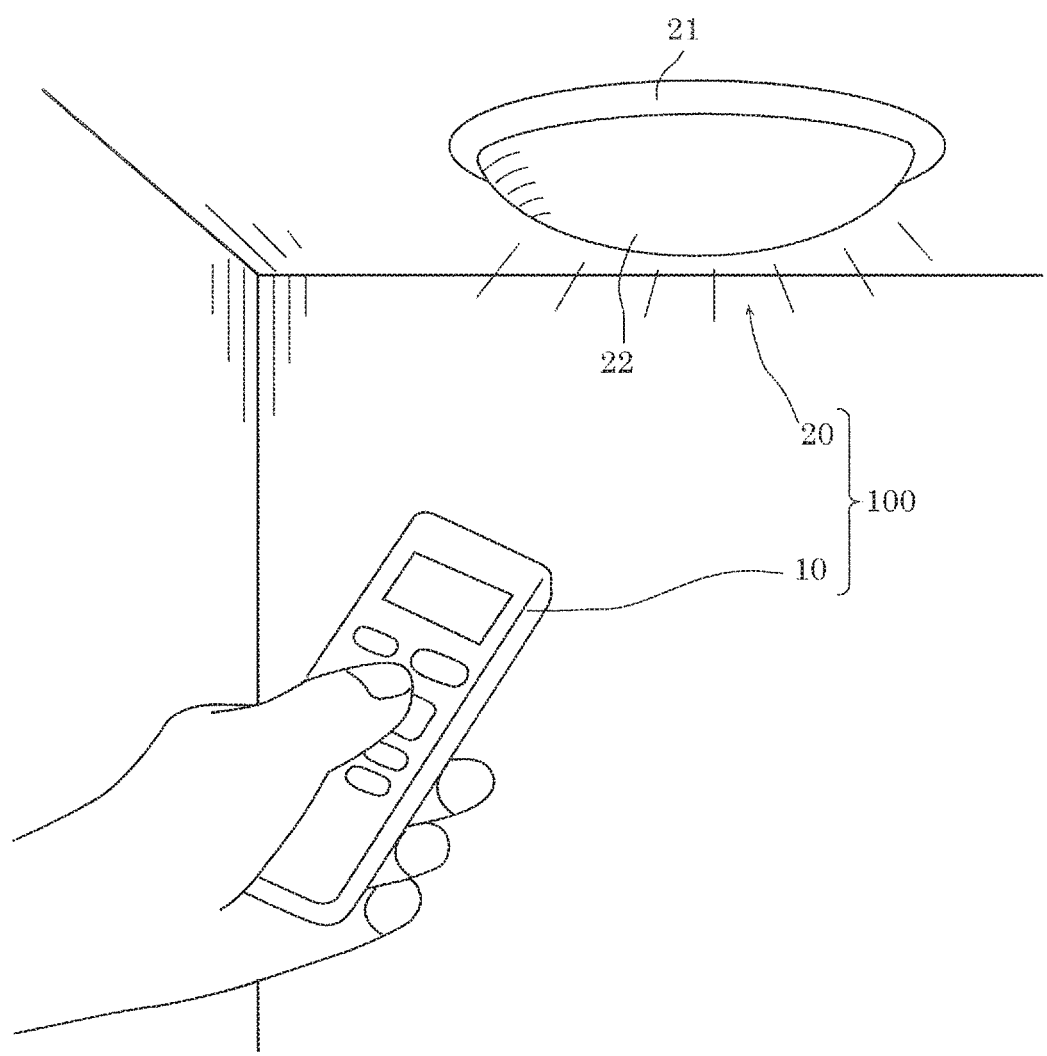
FIG. 1 is a diagram illustrating an overview of an illumination system according to Embodiment 1.
Figure 2:
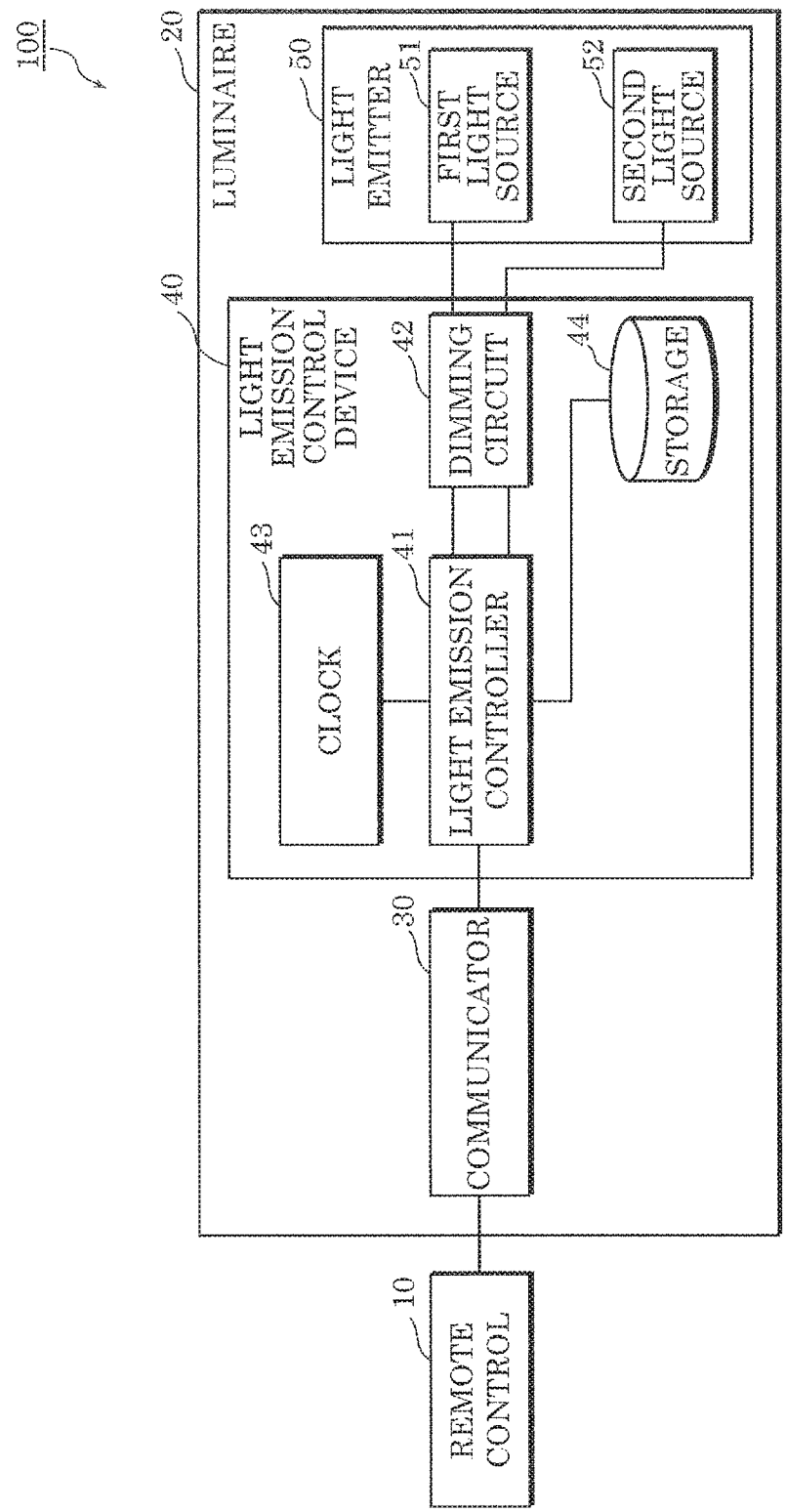
FIG. 2 is a block diagram illustrating a functional configuration of the illumination system according to Embodiment 1.

The following describes a configuration of an illumination system according to Embodiment 1. FIG. 1 is a diagram illustrating an overview of the illumination system according to Embodiment 1. FIG. 2 is a block diagram illustrating a functional configuration of the illumination system according to Embodiment 1.

As illustrated in FIG. 1 and FIG. 2, illumination system 100 according to Embodiment 1 includes remote control 10 and luminaire 20. In illumination system 100, a user can switch (select) between causing luminaire 20 to operate in a normal mode and causing luminaire 20 to operate in a wake-up mode, by using remote control 10. Here, the normal mode is a mode in which luminaire 20 emits light having a color temperature and luminance according to an instruction of the user. The wake-up mode is a mode in which luminaire 20 emits light at gradually increasing luminance over time to wake up a sleeping user.

[Remote Control]

Remote control 10 is a device serving as an operation receiver which receives an operation by the user, in illumination system 100. For example, the user can instruct a color temperature and luminance of luminaire 20 in the normal mode to luminaire 20, by using remote control 10. Moreover, the user can instruct a wake-up time (a time at which the user desires to wake up) in the wake-up mode to luminaire 20, by using remote control 10.

Specifically, remote control 10 is a dedicated controller which is for luminaire 20 and includes, as a receiver, a hardware button which receives an operation by the user. Remote control 10 is not limited to the dedicated controller, and may be an information terminal (a mobile terminal) such as a smartphone and a tablet, or may be another device.

[Luminaire]

Luminaire 20 is a ceiling light which is attached to a ceiling and illuminates a room. As illustrated in FIG. 1, luminaire 20 is a ceiling light having a circular plan view shape, and includes base 21 having a circular plan view shape and dome globe 22 having a circular dome shape. Luminaire 20 is not limited to the ceiling light having the circular plan view shape, and may be an elongated ceiling light or may be a downlight, a spotlight, or the like.

Luminaire 20 is a luminaire which allows dimming (luminance adjustment) and toning (color temperature adjustment), and luminance and a color temperature of white light emitted by luminaire 20 are adjustable. As illustrated in FIG. 2, specifically, luminaire 20 includes communicator 30, light emission control device 40, and light emitter 50. These structural components are housed in an outer case (case) of luminaire 20 including base 21 and globe 22.

[Luminaire: Communicator]

First, the following describes communicator 30. Communicator 30 is an exemplary obtainer, and receives (obtains) an instruction (an instruction signal) transmitted from remote control 10, via wireless communication. Communication between remote control 10 and communicator 30 is, for example, infrared communication. In this case, communicator 30 is an infrared optical receiver.

It should be noted that wireless communication between remote control 10 and communicator 30 is not limited to optical communication such as the infrared communication. The wireless communication between remote control 10 and communicator 30 may be, for example, radio communication using communication standards such as Wi-Fi (registered trademark), Zigbee (registered trademark), and Bluetooth (registered trademark). In this case, communicator 30 is a wireless communication module (a wireless communication circuit) for radio communication. Moreover, the communication between remote control 10 and communicator 30 may be wire communication. In this case, communicator 30 is a wire communication module (a wire communication circuit) for wire communication.

[Luminaire: Light Emission Control Device]

Next, the following describes light emission control device 40. Light emission control device 40 includes light emission controller 41, dimming circuit 42, clock 43, and storage 44.

Light emission controller 41 controls light emission of light emitter 50 by outputting a control signal to dimming circuit 41 based on an instruction signal obtained by communicator 30. Specifically, light emission controller 41 outputs a control signal such as a pulse width modulation (PWM) signal to dimming circuit 42. Specifically, light emission controller 41 is a microcomputer, but may be implemented as a processor or a dedicated communication circuit. Light emission controller 41 may be implemented as a combination of at least two of the microcomputer, the processor, and the dedicated communication circuit.

It should be noted that light emission controller 41 is capable of separately controlling light emission of first light source 51 and second light source 52. Light emission controller 41 outputs a first control signal for controlling light emission of first light source 51, and a second control signal for controlling light emission of second light source 52.

Moreover, light emission controller 41 performs normal control for causing luminaire 20 to operate in the normal mode, and wake-up control for causing luminaire 20 to operate in the wake-up mode. For example, the normal control and the wake-up control are selectively performed. The normal control and the wake-up control will be described in detail later.

Dimming circuit 42 is a circuit which supplies power to light emitter 50 according to a control signal outputted from light emission controller 41. For example, dimming circuit 42 is a chopper control circuit. Light emission controller 41 varies a current supplied to light emitter 50 by switching a switching element included in dimming circuit 42 (chopper control circuit) with the control signal.

More specifically, dimming circuit 42 supplies current to first light source 51 based on the first control signal outputted from light emission controller 41, and supplies current to second light source 52 based on the second control signal outputted from light emission controller 41. Luminance of light emitter 50 is adjusted without varying a color temperature of the same, by varying the current supplied to first light source 51 and the current supplied to second light source 52 while a current ratio therebetween is kept constant. In other words, light emitter 50 is dimmed. Moreover, when the current ratio between the current supplied to first light source 51 and the current supplied to second light source 52 is varied, the color temperature of light emitter 50 is adjusted. In other words, light emitter 50 is toned.

Clock 43 is a clocking device which keeps time, and notifies light emission controller 41 of the time kept by clock 43. Clock 43 is used in the wake-up mode. Specifically, clock 43 is a real-time clock IC etc., and may have any configuration.

Storage 44 is a storage device which stores, for example, a control program executed by light emission controller 41. Storage 44 stores, for example, dimming table information (toning table information) which is for diming (toning) light emitter 50 and in which instruction values of an instruction signal and duty cycles of a control signal are associated with each other, and brightening pattern information (information in which elapsed times and duty cycles of a control signal are associated with each other) used for the wake-up control.

Specifically, storage 44 is implemented as a semiconductor memory etc. It should be noted that when light emission controller 41 is implemented as the microcomputer, storage 44 may be included in light emission controller 41.

[Luminaire: Light Emitter]

Next, the following describes light emitter 50. Light emitter 50 is a light-emitting module which serves as a light source of luminaire 20. Light emitter 50 is, for example, a chip-on-board (COB) light-emitting module which emits white light because blue LED chips mounted on a board are sealed with a light-transmissive resin material containing a phosphor. Light emitter 50 may be a surface-mount device (SMD) light-emitting module in which LED elements which emit white light and have an SMD structure are mounted on a board.

Light emitter 50 includes first light source 51 and second light source 52 which are two light sources differing in color temperature. In light emitter 50, a color temperature of light emitted from light emitter 50 is varied by changing a balance between luminance of first light source 51 and luminance of second light source 52.

When light emitter 50 is the COB light-emitting module, for example, first light source 51 has a configuration in which at least one blue LED chip is sealed with a first light-transmissive resin material, and second light source 52 has a configuration in which at least one blue LED chip is sealed with a second light-transmissive resin material. In this case, the first light-transmissive resin material and the second light-transmissive resin material contain a yellow phosphor and a red phosphor, but differ in phosphor content ratio. In consequence, first light source 51 and second light source 52 differing in color temperature are achieved.

When light emitter 50 is the SMD light-emitting module, first light source 51 includes at least one first SMD LED element, and second light source 52 includes at least one second SMD LED element. When the at least one first SMD LED element and the at least one second SMD LED element differ in color temperature, first light source 51 and second light source 52 differing in color temperature are achieved.

Second light source 52 emits light having a color temperature higher than a color temperature of light emitted by first light source 51. For example, the color temperature of the light emitted by first light source 51 is at most 3000 K, and the color temperature of the light emitted by second light source 52 is at least 5000 K. In Embodiment 1, a color temperature of light emitted by first light source 51 is denoted as a first color temperature, and a color temperature of light emitted by second light source 52 is denoted as a second color temperature.

[Normal Mode (Normal Control)]

Figure 3:
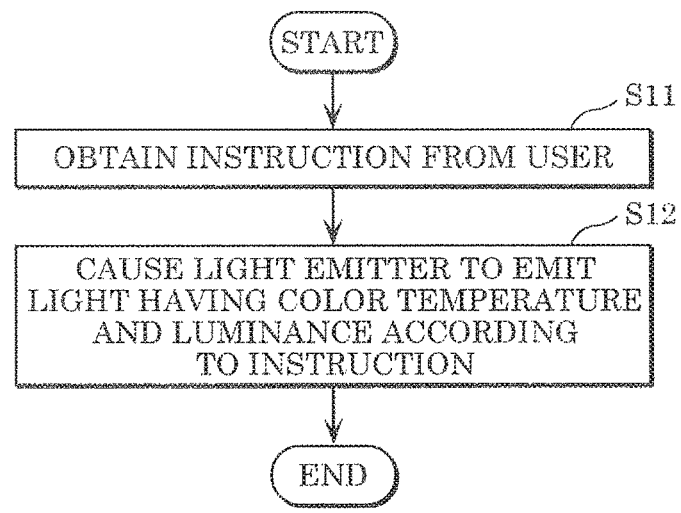
FIG. 3 is a flow chart for normal control according to Embodiment 1.

Next, the following describes the normal control for causing luminaire 20 to operate in the normal mode. FIG. 3 is a flow chart for the normal control.

First, communicator 30 obtains an instruction of a user from remote control 10 (S11). Next, light emission controller 41 causes light emitter 50 to emit light having a color temperature and luminance according to the instruction obtained (S12). Specifically, light emission controller 41 identifies duty cycles of control signals (a first control signal and a second control signal) according to an instruction value of an instruction signal and a dimming table (a toning table) stored in storage 44, and outputs the duty cycles of the control signals identified, to dimming circuit 42. Accordingly, light emitter 50 emits light having the color temperature and the luminance according to the instruction of the user.

Figure 4:
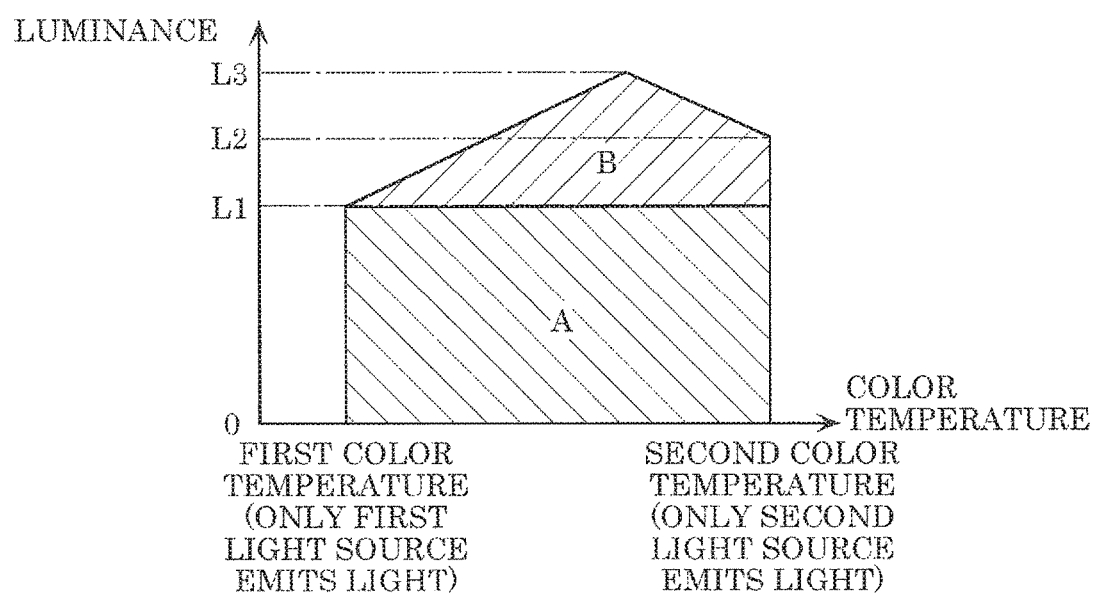
FIG. 4 is a graph illustrating ranges of luminance and color temperature of a light emitter which a user can designate in the normal mode.

Ranges of luminance and a color temperature of light emitter 50 which the user can designate in the normal mode are as illustrated in FIG. 4. FIG. 4 is a graph illustrating the ranges of the luminance and the color temperature of light emitter 50 which the user can designate in the normal mode. The horizontal axis of FIG. 4 represents color temperature, and the vertical axis of FIG. 4 represents luminance.

As illustrated in FIG. 4, the user can designate luminance and a color temperature of light emitter 50 within range A in the normal mode. Specifically, range A is a range in which luminance is at least 0 and at most L1 and a color temperature is at least the first color temperature and at most the second color temperature. It should be noted that the first color temperature is achieved by, out of first light source 51 and second light source 52, first light source 51 emitting light, and the second color temperature is achieved by, out of first light source 51 and second light source 52, second light source 52 emitting light.

Light emitter 50 actually has a capability of emitting light having luminance greater than luminance L1. Specifically, light emitter 50 has a capability of emitting light having luminance and a color temperature within range B illustrated in FIG. 4. The maximum luminance within range B is luminance L3. As is clear from the shape of range B, however, light emitter 50 is not capable of emitting light having any color temperature between the first color temperature and the second color temperature and luminance increased to luminance L3.

For example, in range B, when a color temperature of light gets closer to the first color temperature, the maximum luminance of the light is reduced. Light having the first color temperature never has luminance greater than luminance L1. Likewise, when a color temperature of light gets closer to the second color temperature, the maximum luminance of the light is reduced. Light having the second color temperature never has luminance greater than luminance L2. Light emitter 50 is capable of emitting light having luminance increased to luminance L3 as long as the light has a specific color temperature.

In view of this, in order to equalize the maximum luminance of light having any color temperature, illumination system 100 is configured in such a manner that the luminance and the color temperature within range B cannot be designated by the user (cannot be designated with remote control 10).

[Wake-up Mode (Wake-up Control)]

Figure 5:
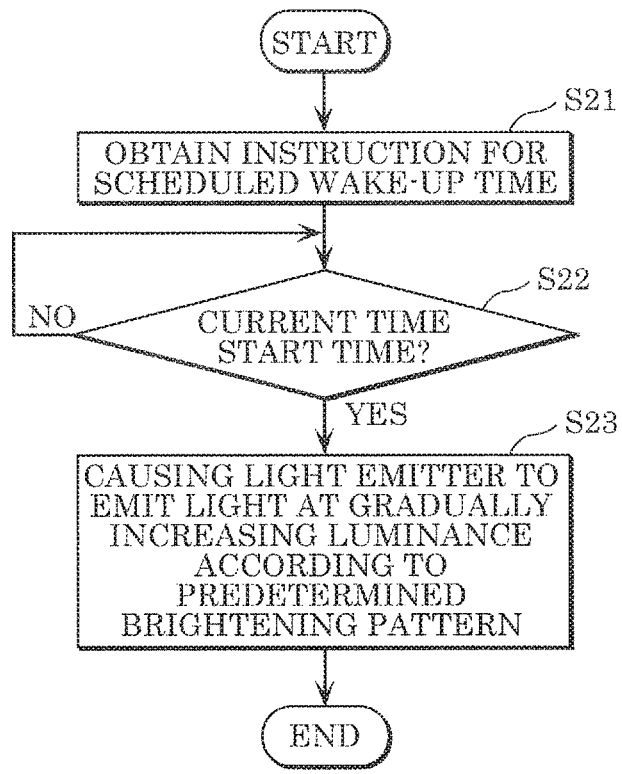
FIG. 5 is a flow chart for wake-up control according to Embodiment 1.

Next, the following describes the wake-up control for causing luminaire 20 to operate in the wake-up mode. FIG. 5 is a flow chart for the wake-up control.

First, communicator 30 obtains an instruction for scheduled wake-up time of a user from remote control 10 (S21). Next, by monitoring the current time notified by clock 43, light emission controller 41 determines whether the current time is a start time which is a time preceding the scheduled wake-up time by a predetermined period (S22). This determination is continuously made until, for example, the current time is the start time (No in S22). The predetermined period is, for example, 1 hour, but is not particularly limited. Moreover, communicator 30 may obtain an instruction for the length of the predetermined period from remote control 10 in step S21. In other words, the length of the predetermined period (a start time for the wake-up control) may be designated by the user.

Figure 6:
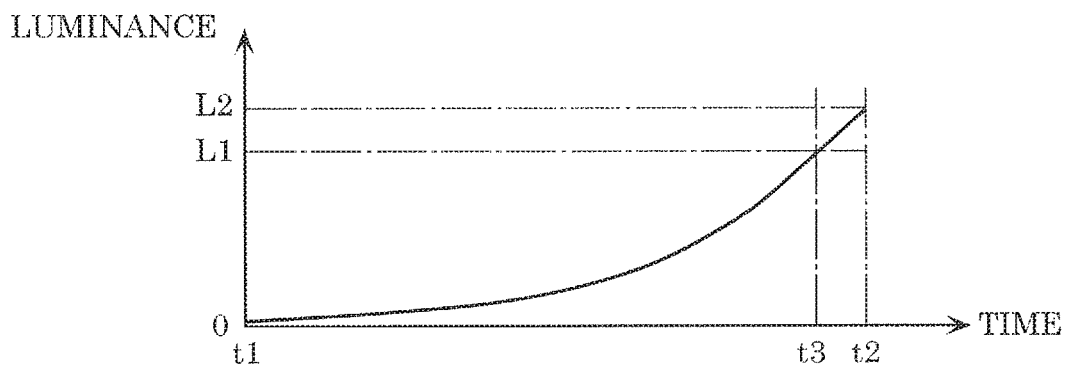
FIG. 6 is a graph illustrating luminance of the light emitter in the wake-up control according to Embodiment 1.

When light emission controller 41 determines that the current time is the start time (Yes in S22), light emission controller 41 starts the wake-up control. Specifically, light emission controller 41 causes light emitter 50 to emit light at gradually increasing luminance over time according to a predetermined brightening pattern (along with the predetermined brightening pattern). FIG. 6 is a graph illustrating luminance of light emitter 50 in the wake-up control.

As illustrated in FIG. 6, when the current time is start time t1, light emission controller 41 causes light emitter 50 to emit light at gradually increasing luminance from start time t1 to scheduled wake-up time t2. Because the wake-up control is control for waking up a sleeping user, the luminance of light emitter 50 may be as maximum as possible. In contrast, because the wake-up control is performed while the user is sleeping, unlike in the normal control, there is less need to equalize the maximum luminance of light having any color temperature in the wake-up control.

For this reason, in the final phase of the wake-up control (a period between time t3 and scheduled wake-up time t2 in FIG. 6), light emission controller 41 allows luminance and color temperatures within range B in FIG. 4 which are prohibited in the normal control, and causes light emitter 50 to emit light having at least luminance L1 (luminance and a color temperature within range B).

As above, the maximum luminance of light emitted by light emitter 50 in the wake-up control is greater than the maximum luminance of the light emitted by light emitter 50 in the normal control. Accordingly, luminaire 20 (illumination system 100) makes it possible to effectively wake up the user by the wake-up control in which light having luminance greater than luminance of light emitted in the normal control is emitted.

It should be noted that a color temperature of the light emitted by light emitter 50 in the wake-up control is not particularly limited, and light emitter 50 may be caused to emit light at gradually increasing luminance in the wake-up control. Although, for example, light emitter 50 emits light having a single color temperature from start time t1 to scheduled wake-up time t2, a color temperature of light emitted by light emitter 50 in a period from start time t1 to time t3 may be different from a color temperature of light emitted by light emitter 50 in a period from time t3 to scheduled wake-up time t2.

For example, light emission controller 41 causes first light source 51 and second light source 52 to emit light in the period from start time t1 to time t3, and causes second light source 52 to emit light in the period from time t3 to scheduled wake-up time t2. In other words, for example, light emission controller 41 achieves luminance prohibited in the normal control (luminance greater than luminance L1 and less than luminance L3 (illustrated in FIG. 4)), by causing, out of first light source 51 and second light source 52, second light source 52 to emit light. It should be noted that light emission controller 41 may achieve the luminance prohibited in the normal control, by causing second light source 52 to emit light having luminance greater than luminance of light emitted by first light source 51.

When second light source 52 is caused to emit light in the period from time t3 to scheduled wake-up time t2, the maximum luminance of the light emitted by light emitter 50 in the wake-up control is luminance L2 which is greater than luminance L1 and less than luminance L3 (illustrated in FIG. 4).

It should be noted that the maximum luminance of the light emitted by light emitter 50 in the wake-up control may be luminance L3, and a color temperature of the light emitted by light emitter 50 in this case is a specific color temperature which allows an increase to luminance 3 in FIG. 4.

It is generally known that exposing a person to light having a high color temperature (light similar to blue light) causes the person to decrease secretion of melatonin and shake off drowsiness. Accordingly, it is possible to allow the user to wake up comfortably when light emitter 50 emits light having the second color temperature which is relatively high, in the final phase of the wake-up control.

[Variation]

Figure 7:
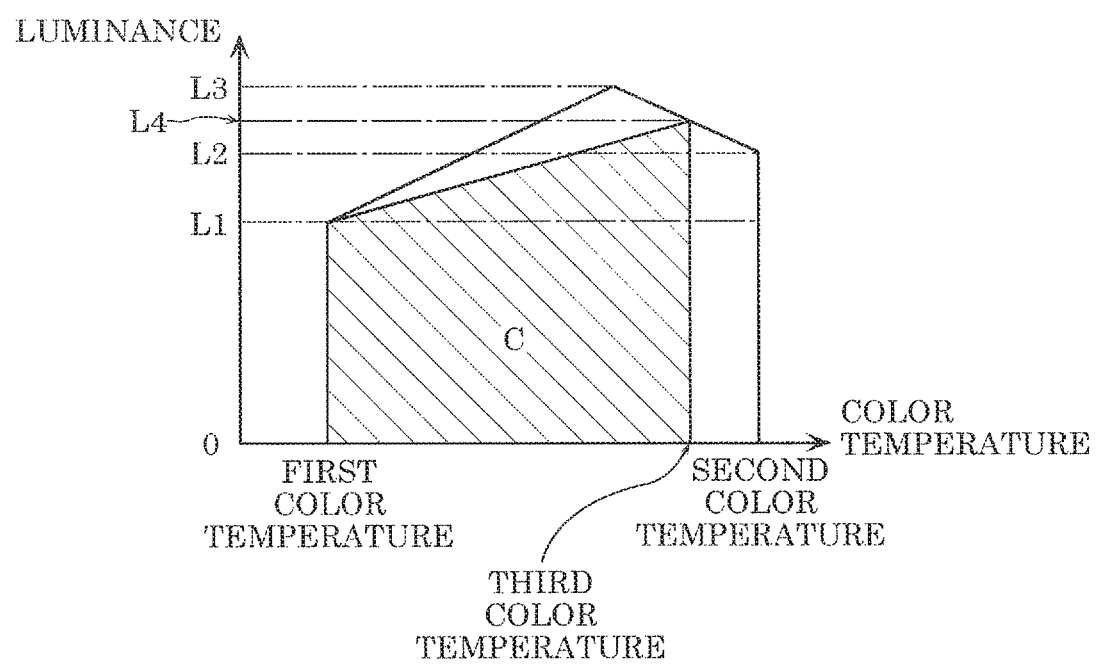
FIG. 7 is a graph illustrating another exemplary range of luminance and color temperature of the light emitter which a user can designate in the normal mode.

Although the user can designate, in the normal mode, the luminance and the color temperature of light emitter 50 within range A in FIG. 4, the luminance and the color temperature of light emitter 50 that the user can designate in the normal mode are not limited to range A. For example, the user may be able to designate, in the normal mode, luminance and a color temperature within range C illustrated in FIG. 7. FIG. 7 is a graph illustrating another exemplary range of luminance and a color temperature of light emitter 50 which the user can designate in the normal mode.

Range C illustrated in FIG. 7 is a range in which a color temperature is at least the first color temperature and at most a third color temperature. In range C, the maximum luminance linearly increases with an increase in color temperature. The third color temperature is lower than the second color temperature, and is, for example, 6200 K. The maximum luminance at the first color temperature is luminance L1, and the maximum luminance at the third color temperature is luminance L4. Luminance L4 is less than luminance L3 and greater than luminance L2.

Even when the luminance and the color temperature of light emitter 50 that the user can designate in the normal mode are within range C, the maximum luminance of light emitted by light emitter 50 in the wake-up control may be greater than the maximum luminance of light emitted by light emitter 50 in the normal control. Specifically, light emission controller 41 may cause light emitter 50 to emit light having at least luminance L4 (e.g., luminance L3), in the final phase of the wake-up control. Accordingly, illumination system 100 makes it possible to effectively wake up the user.

It should be noted that when the maximum luminance of the light emitted by light emitter 50 in the wake-up control is greater than the maximum luminance of the light emitted by light emitter 50 in the normal control, power consumption increases more in the wake-up control than in the normal control. In view of this, a time may be limited for which light emitter 50 emits light having the maximum luminance in the wake-up control.

For example, light emission controller 41 may limit a time for which light emitter 50 emits light having the maximum luminance, using clock 43. Moreover, for example, light emission control device 40a may further include a temperature sensor, and may dim light emitter 50 in the case where a temperature of light emitter 50 reaches a predetermined temperature when light emitter 50 emits light having the maximum luminance.

[Advantageous Effects Etc.]

As described above, in illumination system 100 (luminaire 20), light emission control device 40 includes light emission controller 41 which controls light emitter 50 and performs normal control and wake-up control, the normal control being control for causing light emitter 50 to emit light having a color temperature and luminance according to an instruction of a user, the wake-up control being control for causing light emitter 50 to emit light at increasing luminance over time to wake up the user who is sleeping. The maximum luminance of light emitted by light emitter 50 in the wake-up control is greater than the maximum luminance of the light emitted by light emitter 50 in the normal control.

With this, luminaire 41 (illumination system 100) makes it possible to effectively wake up the user by the wake-up control in which light having luminance greater than luminance of light emitted in the normal control is emitted.

Moreover, light emitter 50 may include first light source 51 and second light source 52 which emits light having a color temperature higher than a color temperature of light emitted by first light source 51. In the wake-up control, light emission controller 41 may cause light emitter 50 to emit light having luminance greater than the maximum luminance of the light emitted by light emitter 50 in the normal control, by causing second light source 52 to emit brighter light than first light source 51.

With this, light emission controller 41 allows the user to wake up comfortably because light emitter 50 emits light having a color temperature similar to a second color temperature relatively suitable for waking up, in the final phase of the wake-up control in which light emitter 50 emits light having luminance greater than luminance of light emitted in the normal control.

In the wake-up control, light emission controller 41 may cause light emitter 50 to emit light having luminance greater than the maximum luminance of the light emitted by light emitter 50 in the normal control, by causing, out of first light source 51 and second light source 52, second light source 52 to emit light.

With this, light emission controller 41 allows the user to wake up comfortably because light emitter 50 emits light having the second color temperature relatively suitable for waking up, in the final phase of the wake-up control in which light emitter 50 emits light having luminance greater than luminance of light emitted in the normal control.

Moreover, the light emitted by first light source 51 may be at most 3000 K, and the light emitted by second light source 52 may be at least 5000 K.

With this, light emitter 50 is capable of emitting light having a first color temperature of at most 3000 K, which produces an effect of reducing a decrease in secretion of melatonin and is suitable for sleeping, and light having the second color temperature of at least 5000 K, which produces an effect of decreasing the secretion of melatonin and is suitable for waking up.

Moreover, the present disclosure may be realized as an electronic device including light emission control device 40 and a case housing light emission control device 40. Specifically, the electronic device is, for example, luminaire 20 further including light emitter 50. It should be noted that in this case, the case includes base 21 and globe 22.

Such an electronic device (luminaire 20) produces the same advantageous effects as light emission control device 40. It should be noted that the present disclosure may be realized as an electronic device other than luminaire 20. Such an electronic device is, for example, remote control 10 including a light emission controller capable of substantially performing control on light emitter 50 in a similar manner as light emission controller 41. Such an electronic device may also be a smartphone or an information terminal such as a tablet which includes a light emission controller capable of substantially performing control on light emitter 50 in a similar manner as light emission controller 41, by a dedicated application being installed therein. Furthermore, the present disclosure may be realized as another electronic device having an illumination function.

(Embodiment 2)
[Entire Configuration]

Boost control in which luminance is more rapidly increased than usual may be performed in the wake-up control. In this case, start timing of the boost control may be determined according to a sleep state of a user.

Figure 8:
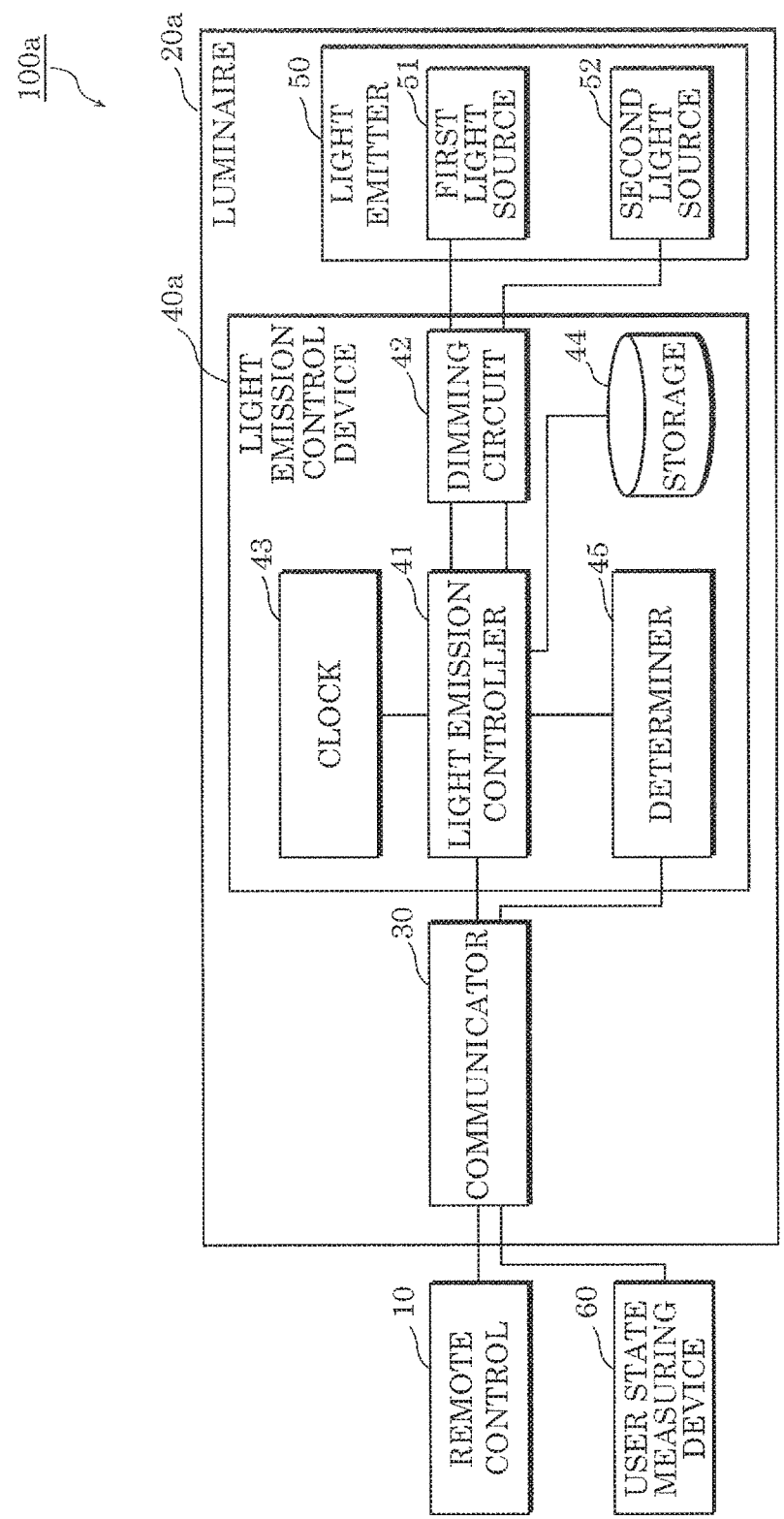
FIG. 8 is a block diagram illustrating a functional configuration of an illumination system according to Embodiment 2.

The following describes a configuration of an illumination system according to Embodiment 2 which is capable of performing such boost control. FIG. 8 is a block diagram illustrating a functional configuration of the illumination system according to Embodiment 2. It should be noted that the following description of Embodiment 2 will be centered on differences from Embodiment 1, and description of matters already described in Embodiment 1 will be omitted or simplified.

As illustrated in FIG. 8, illumination system 100a according to Embodiment 2 includes user state measuring device 60 in addition to remote control 10 and luminaire 20a.

[User State Measuring Device]

User state measuring device 60 is a device which directly or indirectly measures a state of the user. User state measuring device 60 is, for example, an activity sensor including an acceleration sensor or a gyroscope sensor, is attached to a wrist of the user, and measures an activity amount of the user as information indicating a state of the user (user state information). Although the activity amount measured by user state measuring device 60 is transmitted to communicator 30 via, for example, wireless communication, the activity amount measured by user state measuring device 60 may be transmitted to communicator 30 via wire communication.

It should be noted that user state measuring device 60 may be a brain wave sensor, an eye potential sensor which measures an eye movement, a myoelectric potential sensor which measures myoelectric activity, a blood pressure sensor, a respiration sensor, a heart rate sensor, or a pulse rate sensor.

It should be noted that although user state measuring device 60 is basically a contact sensor attached to (equipped by) the user, user state measuring device 60 may be a non-contact sensor which performs sensing without contacting the user. For example, a respiratory rate, a pulse rate, a heart rate, and a body motion amount are obtainable by a radio-frequency sensor which transmits radio waves toward the user. In other words, user state measuring device 60 may be the radio-frequency sensor.

[Luminaire: Determiner]

Light emission control device 40a included in luminaire 20a differs from light emission control device 40 in including determiner 45.

Figure 9:
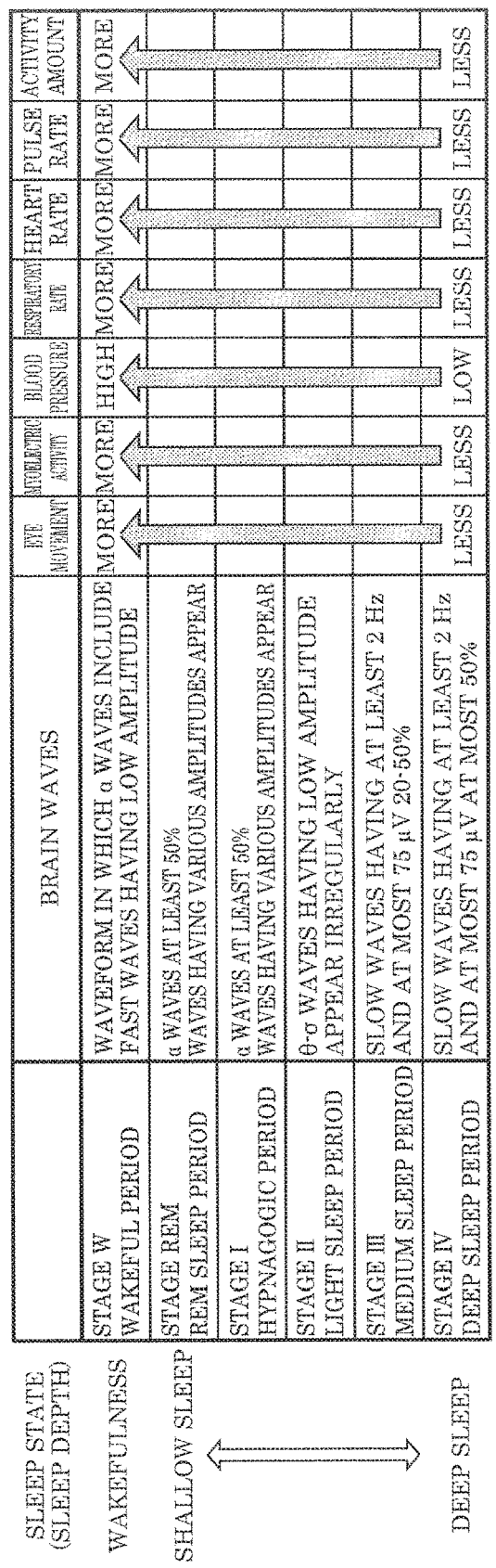
FIG. 9 is a diagram illustrating exemplary criteria for a sleep state.

Determiner 45 determines in real time a sleep state (sleep depth) of the user based on user state information obtained by communicator 30. When the user state information is an activity amount, determiner 45 determines the sleep state as shallower sleep with an increase in activity amount, and the sleep state as deeper sleep with a decrease in activity amount. FIG. 9 is a diagram illustrating exemplary criteria for a sleep state.

As illustrated in FIG. 9, determiner 45 is capable of determining, for example, which one of six stages the sleep state of the user is, by comparing the obtained activity amount and a predetermined threshold, the six stages including a wakeful period (stage Wake), a REM sleep period, a hypnagogic period (stage 1), a light sleep period (stage 2), a medium sleep period (stage 3), and a deep sleep period (stage 4). Even when the user state information is brain waves, an eye movement, myoelectric activity, a blood pressure, a respiration rate, a heart rate, or a pulse rate, determiner 45 is capable of determining which one of the six stages the sleep state of the user is according to such criteria as illustrated in FIG. 9.

As described later, specifically, light emission controller 41 starts the boost control when the sleep state of the user becomes a state other than a REM sleep state (a state included in the REM sleep period). For this reason, specifically, determiner 45 determines whether the user is in the REM sleep state.

Specifically, determiner 45 is a microcomputer, but may be implemented as a processor or a dedicated communication circuit. Determiner 45 may be implemented as a combination of at least two of the microcomputer, the processor, and the dedicated communication circuit.

It should be noted that the above-mentioned six stages of the sleep state (sleep stages) are defined based on a sleep stage determination method using polysomnography (PSG). For example, the International 10-20 system of Reftshaffen and Kales is used for determining a sleep stage based on brain waves.

[First Example of Wake-up Control According to Embodiment 2]

Figure 10:
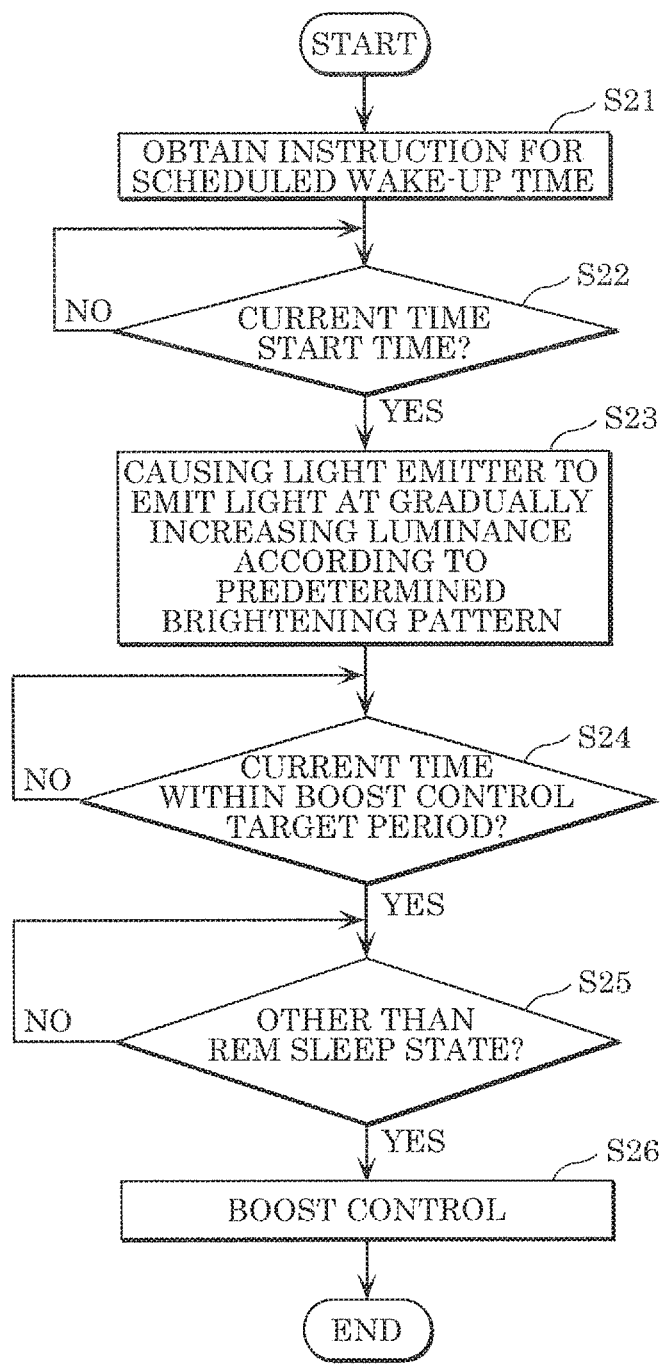
FIG. 10 is a flow chart for a first example of wake-up control according to Embodiment 2.

Next, the following describes a first example of the wake-up control (the wake-up control including the boost control) according to Embodiment 2. FIG. 10 is a flow chart for the first example of the wake-up control according to Embodiment 2.

Like in Embodiment 1, communicator 30 obtains an instruction for scheduled wake-up time t2 of a user from remote control 10 (S21), and light emission controller 41 determines whether the current time is start time t1 (S22). This determination is continuously made until, for example, the current time is start time t1(No in S22).

When light emission controller 41 determines that the current time is start time t1(Yes in S22), light emission controller 41 starts the wake-up control. Specifically, light emission controller 41 causes light emitter 50 to emit light at gradually increasing luminance over time according to a predetermined brightening pattern (S23).

Figure 11:
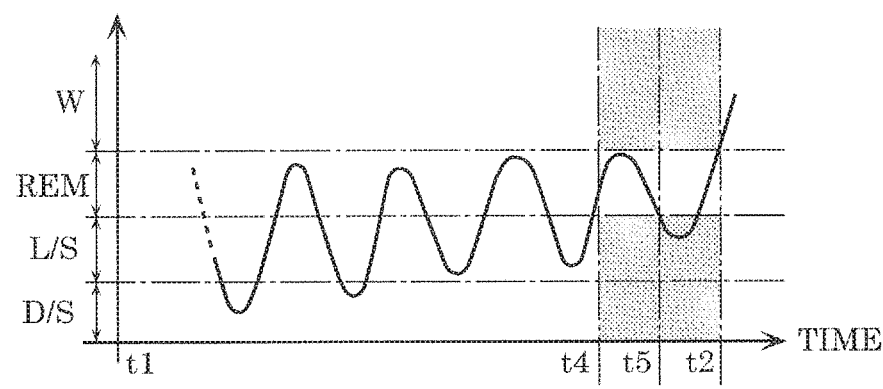
FIG. 11 is a graph illustrating a sleep state and luminance of a light emitter in the first example of the wake-up control according to Embodiment 2.
Figure 11:
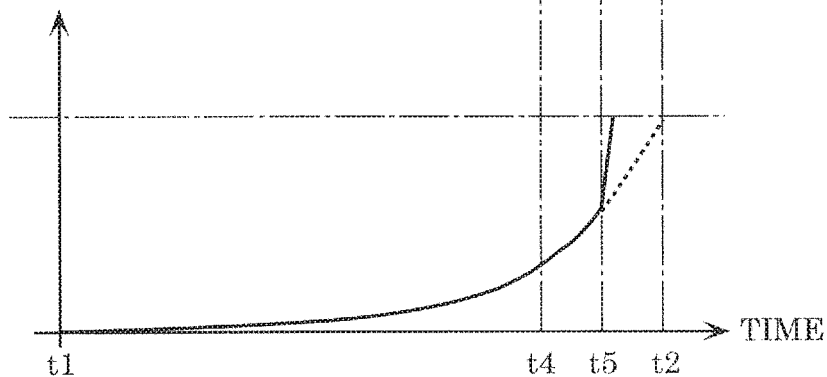

Once the wake-up control is started, light emission controller 41 starts the boost control according to a sleep state determined by determiner 45. FIG. 11 is a graph illustrating a sleep state ((a) of FIG. 11) and luminance of light emitter 50 ((b) of FIG. 11) in the first example of the wake-up control according to Embodiment 2. It should be noted that in (a) of FIG. 11, W denotes a wakeful state (the state included in the wakeful period), and REM denotes s REM sleep state. Moreover, in (a) of FIG. 11, L/S denotes a hypnagogic state and a light sleep state (a state included in the hypnagogic period and the light sleep period), and D/S denotes a medium sleep state and a deep sleep state (a state included in the medium sleep period and the deep sleep period).

In order to surely wake up the user at scheduled wake-up time t2, the boost control is performed in the final phase of the wake-up control, that is, in a predetermined period closest to scheduled wake-up time t2. Stated differently, this predetermined period is a boost control target period and is a period from time t4 to scheduled wake-up time t2 in FIG. 11.

In view of this, after the wake-up control is started, light emission controller 41 determines whether the current time is within the boost control target period (S24). This determination is continuously made until the current time enters the boost control target period (the current time passes time t4) (No in S24). Although the boost control target period is, for example, a 30-minute period ending at scheduled wake-up time t2, the length of the boost control target period is not particularly limited.

The boost control is started at a time (with timing) when determiner 45 first determines that the user is in a state other than the REM sleep state, within the boost control target period (after time t4). For this reason, after the current time is determined to be within the boost control target period (Yes in S24), determiner 45 determines whether the user is in the state other than the REM sleep state (S25). This determination is continuously made at least until the user is in the state other than the REM sleep state (No in S25). It should be noted that examples of the state other than the REM sleep state include the wakeful state and a sleep state deeper than the REM sleep state (the hypnagogic state, the light sleep state, the medium sleep state, and the deep sleep state). In FIG. 9, examples of the state other than the REM sleep state include states denoted by the symbols W, L/S, and D/S.

When determiner 45 determines that the user is in the state other than the REM sleep state (Yes in S25), light emission controller 41 starts the boost control (S26). In the example of FIG. 11, the user is determined to be in the state other than REM sleep state (the sleep state of the user is a state included in any hatched region in (a) of FIG. 11) at time t5. Accordingly, at time t5, light emission controller 41 starts the boost control for causing light emitter 50 to emit light at more steeply increasing luminance than in the predetermined brightening pattern (a broken line in (b) of FIG. 11).

As described above, light emission controller 41 (illumination system 100a) starts the boost control except for the REM sleep state that is a state in which a brain runs wild. With this, it is possible to allow the user to wake up comfortably.

[Second Example of Wake-up Control According to Embodiment 2]

Figure 12:
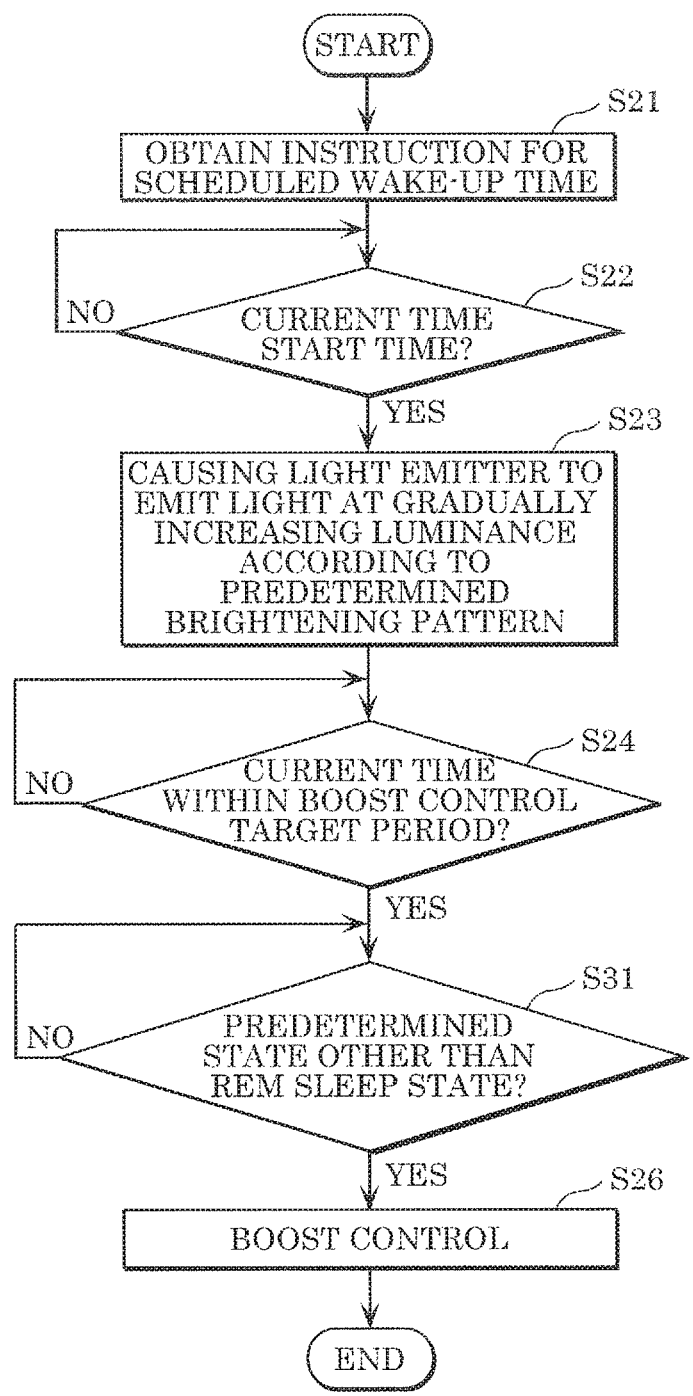
FIG. 12 is a flow chart for a second example of the wake-up control according to Embodiment 2.
Figure 13:
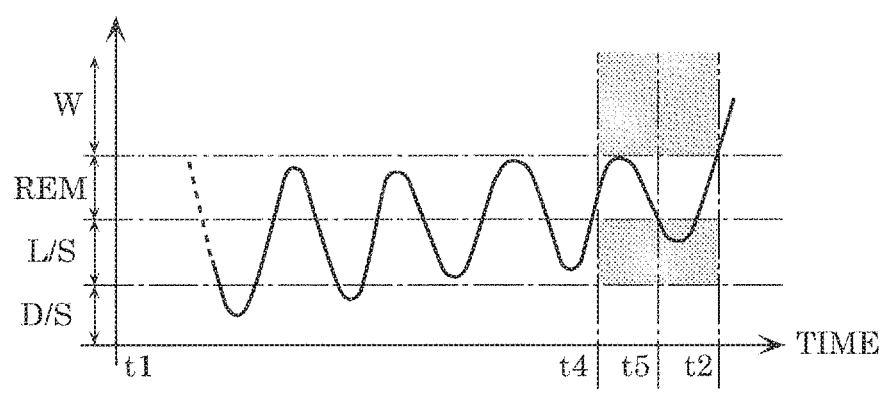
FIG. 13 is a graph illustrating a sleep state and luminance of the light emitter in the second example of the wake-up control according to Embodiment 2.
Figure 13:
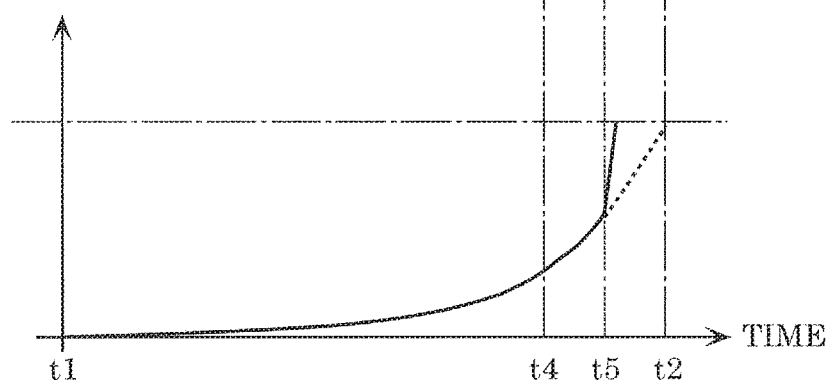

Next, the following describes a second example of the wake-up control according to Embodiment 2. FIG. 12 is a flow chart for the second example of the wake-up control according to Embodiment 2. FIG. 13 is a graph illustrating a sleep state ((a) of FIG. 13) and luminance of light emitter 50 ((b) of FIG. 13) in the second example of the wake-up control according to Embodiment 2. The following description of the second example of the wake-up control according to Embodiment 2 will be centered on differences from the first example of the wake-up control according to Embodiment 2.

In the second example of the wake-up control according to Embodiment 2, after the current time is determined to be within the boost control target period (Yes in S24), determiner 45 determines whether the user is in a predetermined state other than the REM sleep state (S31). Specifically, the predetermined state is any one of the wakeful state, the hypnagogic state, and the light sleep state. In other words, the predetermined state includes the wakeful state and a sleep state deeper than the REM sleep state and shallower than the medium sleep state. The above-mentioned determination is continuously made at least until the user is in the predetermined state other than the REM sleep state (No in S31).

When determiner 45 determines that the user is in the predetermined state other than the REM sleep state (Yes in S31), light emission controller 41 starts the boost control (S26). In the example of FIG. 13, the user is determined to be in the predetermined state other than REM sleep state (the sleep state of the user is a state included in any hatched region in (a) of FIG. 13) at time t5. Accordingly, at time t5, light emission controller 41 starts the boost control for causing light emitter 50 to emit light at more steeply increasing luminance than in the predetermined brightening pattern (a broken line in (b) of FIG. 13).

As described above, light emission controller 41 (illumination system 100*a*) starts the boost control except for the REM sleep state that is a state in which a brain runs wild, and a state in which sleep is too deep (the medium sleep state and the deep sleep state). With this, it is possible to allow the user to wake up comfortably.

[Advantageous Effects Etc. of Embodiment 2]

As described above, in the wake-up control, when light emission controller 41 of illumination system 100*a* according to Embodiment 2 causes light emitter 50 to emit light at increasing luminance over time according to a predetermined brightening pattern, light emission controller 41 further performs boost control, the boost control being control for causing light emitter 50 to emit light at more steeply increasing luminance than in the predetermined brightening pattern.

With this, light emission controller 41 (illumination system 100*a*) makes it possible to increase certainty in waking up the user.

Moreover, light emission control device 40*a* may further include determiner 45 which determines a sleep state of the user. Light emission controller 41 may start the boost control at a time when the user is determined to be in a state other than a REM sleep state.

With this, light emission controller 41 (illumination system 100*a*) allows the user to wake up comfortably because light emission controller 41 starts the boost control except for the REM sleep state that is a state in which a brain runs wild.

Moreover, light emission controller 41 may start the boost control when the user is determined to be in any one of a wakeful state, a hypnagogic state, and a light sleep state.

With this, light emission controller 41 (illumination system 100*a*) allows the user to wake up comfortably because light emission controller 41 starts the boost control except for the REM sleep state and a state in which sleep is too deep.

(Embodiment 3)

Figure 14:
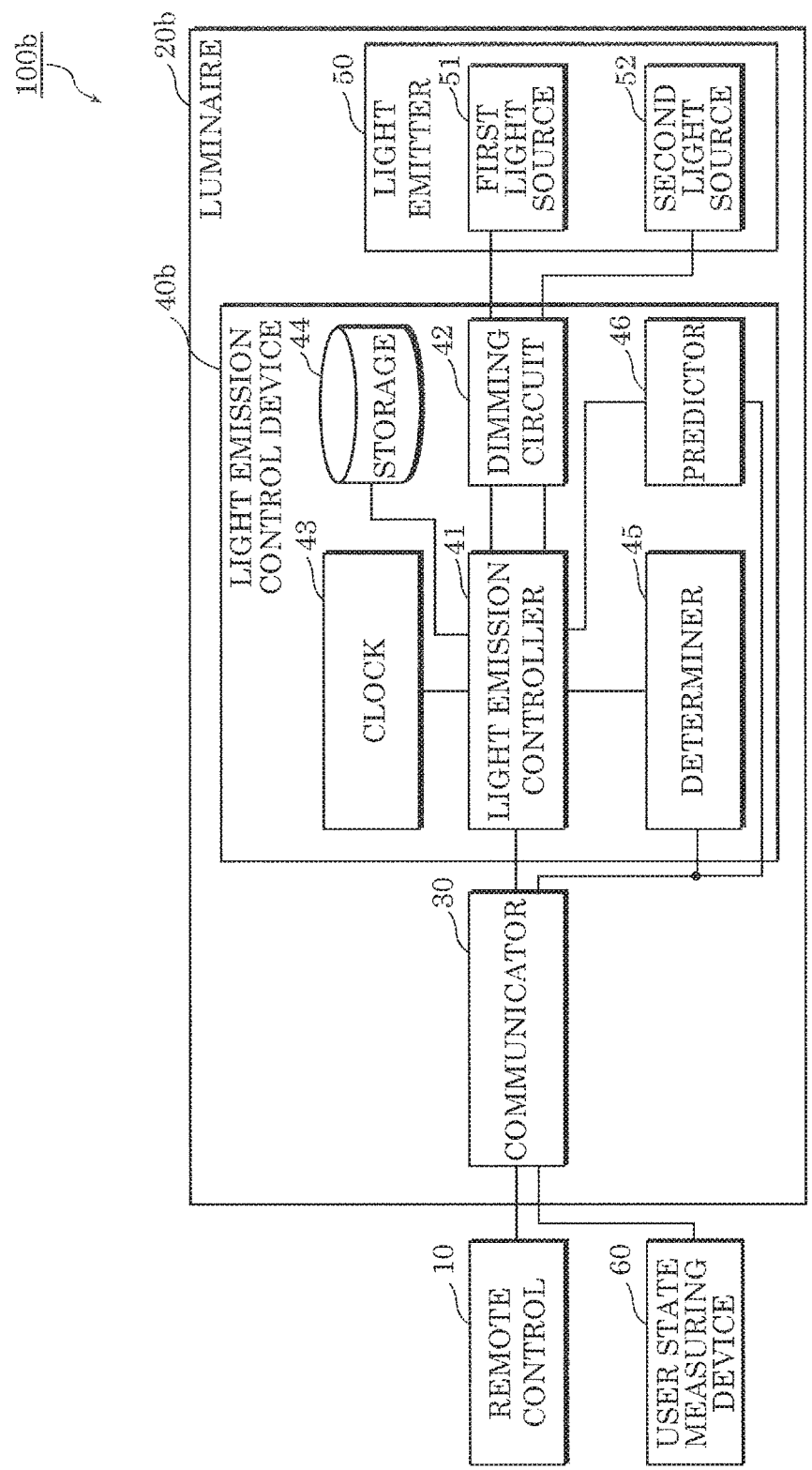
FIG. 14 is a block diagram illustrating a functional configuration of an illumination system according to Embodiment 3.

Start timing of the boost control may be determined based on prediction of a sleep state of a user. The following describes a configuration of an illumination system according to Embodiment 3 which is capable of performing such boost control. FIG. 14 is a block diagram illustrating a functional configuration of the illumination system according to Embodiment 3. It should be noted that the following description of Embodiment 3 will be centered on differences from Embodiments 1 and 2, and description of matters already described in Embodiments 1 and 2 will be omitted or simplified.

As illustrated in FIG. 14, illumination system 100*b* according to Embodiment 3 includes remote control 10, luminaire 20*b*, and user state measuring device 60.

[Luminaire: Predictor]

Light emission control device 40*b* included in luminaire 20*b* differs from light emission control device 40 and light emission control device 40*a* in including predictor 46.

Predictor 46 predicts a change of sleep state (sleep depth) of the user over time based on user state information obtained by communicator 30. Specifically, predictor 46 stores a history of sleep states of the user into storage 44, and predicts the change of sleep state of the user over time based on the stored history of the sleep states.

Predictor 46 predicts, for example, a sleep cycle (a time from peak to peak of a sleep state). Predictor 46 predicts, for example, a sleep cycle from a predetermined time to scheduled wake-up time t2 in a bed period from a bedtime to scheduled wake-up time t2, based on an actual value of a sleep state from the bedtime to the predetermined time. In other words, predictor 46 predicts a future sleep cycle based on a past sleep state.

It should be noted that as described later, it is sufficient that predictor 46 is capable of predicting a time preceding at least scheduled wake-up time t2 by one sleep cycle. In other words, it is sufficient that predictor 46 is capable of predicting the length of one sleep cycle. The length of the one sleep cycle is predicted based on, for example, statistical processing such as processing for calculation of an average value of past sleep cycles. It should be noted that a sleep cycle usually has a length of at least 60 minutes and at most 120 minutes.

Specifically, predictor 46 is a microcomputer, but may be implemented as a processor or a dedicated communication circuit. Predictor 46 may be implemented as a combination of at least two of the microcomputer, the processor, and the dedicated communication circuit.

It should be noted that a device other than luminaire 20*b* may predict a sleep cycle. For example, the device is a cloud server. The device predicts a sleep state based on user state information obtained from user state measuring device 60, stores a history of sleep states into a storage included in the device, and predicts a sleep cycle of the user based on the stored history of the sleep states.

In this case, light emission control device 40*b* of luminaire 20*b* obtains the sleep cycle from the device via communicator 30. For this reason, light emission control device 40*b* need not include predictor 46, and storage 44 of light emission control device 40*b* need not store the history of the sleep states.

[First Example of Wake-up Control According to Embodiment 3]

Figure 15:
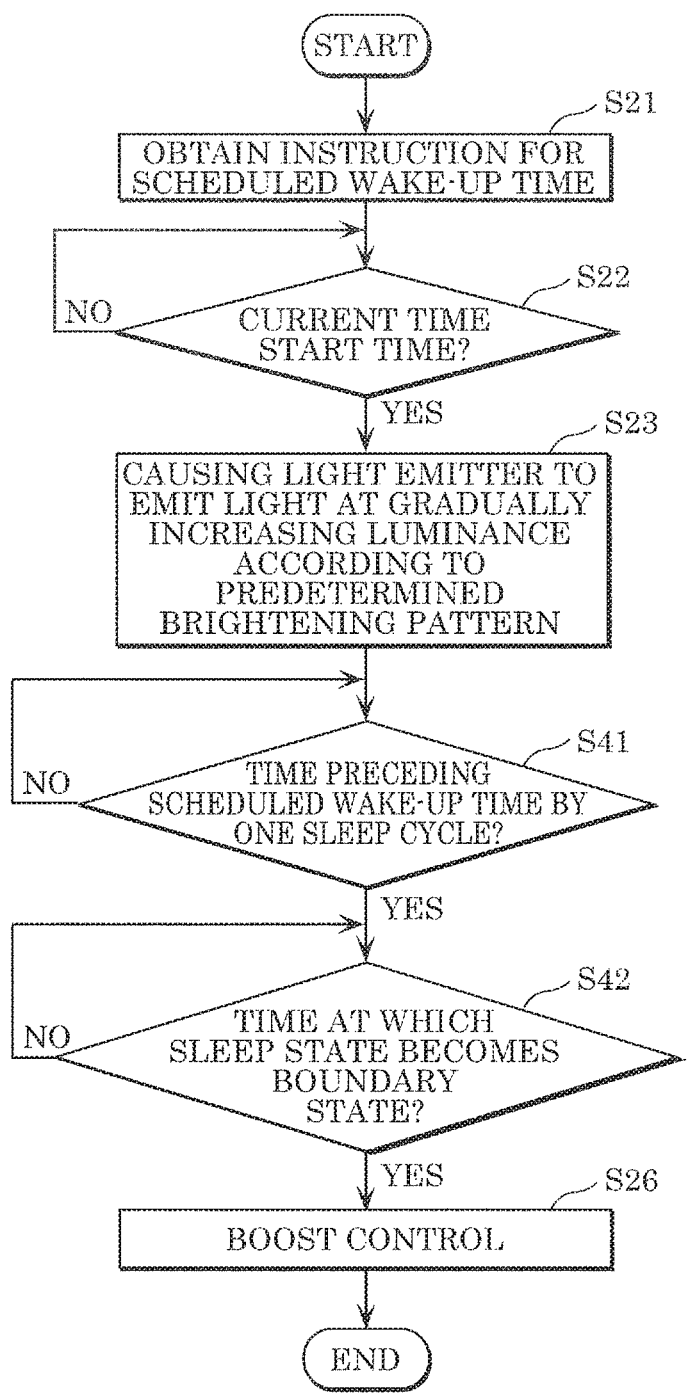
FIG. 15 is a flow chart for a first example of wake-up control according to Embodiment 3.
Figure 16:
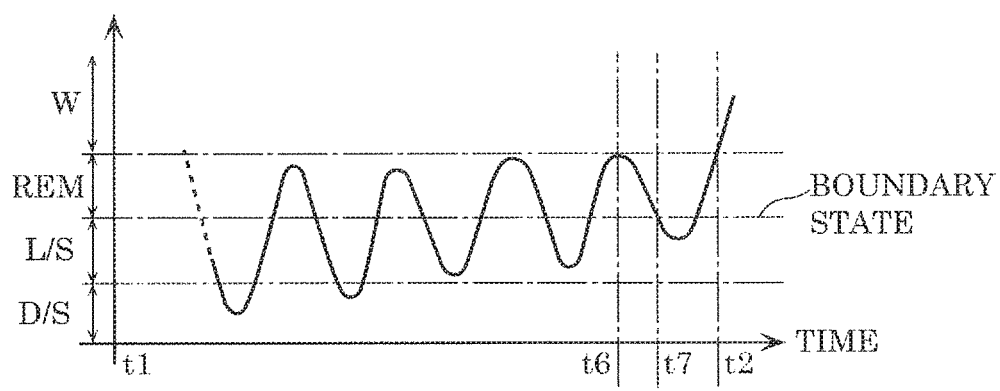
FIG. 16 is a graph illustrating a sleep state and luminance of a light emitter in the first example of the wake-up control according to Embodiment 3.
Figure 16:
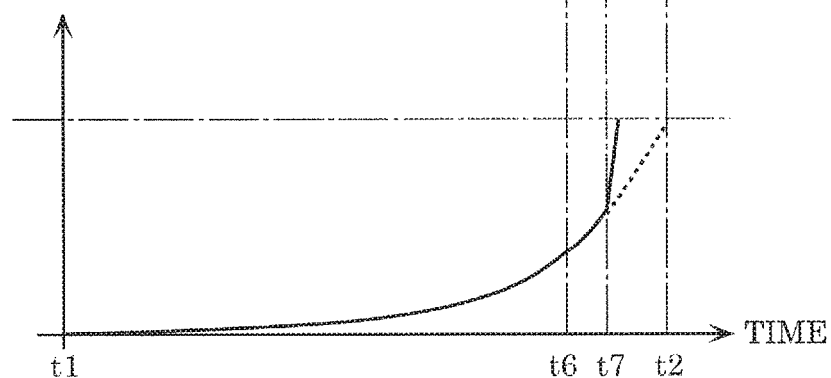

Next, the following describes a first example of the wake-up control according to Embodiment 3. FIG. 15 is a flow chart for the first example of the wake-up control according to Embodiment 3. FIG. 16 is a graph illustrating a sleep state ((a) of FIG. 16) and luminance of light emitter 50 ((b) of FIG. 16) in the first example of the wake-up control according to Embodiment 3. The following description of the first example of the wake-up control according to Embodiment 3 will be centered on differences from the wake-up control according to Embodiment 2.

Like in Embodiment 2, communicator 30 obtains an instruction for scheduled wake-up time t2 of a user from remote control 10 (S21), and light emission controller 41 determines whether the current time is start time t1 (S22). This determination is continuously made until, for example, the current time is start time t1 (No in S22).

When light emission controller 41 determines that the current time is start time t1 (Yes in S22), light emission controller 41 starts the wake-up control. Specifically, light emission controller 41 causes light emitter 50 to emit light at gradually increasing luminance over time according to a predetermined brightening pattern (S23).

Once the wake-up control is started, light emission controller 41 determines whether the current time is time t6 preceding scheduled wake-up time t2 by one sleep cycle (S41). This determination is continuously made until, for example, the current time is start time t6 (No in S41).

When light emission controller 41 determines that the current time is time t6 (Yes in S41), light emission controller 41 determines whether the current time is time t7 which is a time at which the sleep state of the user becomes a boundary state (S42). This determination is continuously made until, for example, the current time is start time t7 (No in S42). It should be noted that time t7 is a time included in a period from time t6 to scheduled wake-up time t2. In other words, time t7 is a time included in one sleep cycle ending at scheduled wake-up time t2. Although time t7 is identified based on the sleep state of the user (an actual value) determined by determiner 45 after time t6, time t7 may be identified based on prediction of a sleep state made by predictor 46.

Specifically, the boundary state is a boundary state between the REM sleep state and a sleep state (specifically the hypnagogic state) deeper than the REM sleep state. It should be noted that the boundary state need not be a strict boundary state, and may be a state close to a boundary between the REM sleep state and the hypnagogic state.

When light emission controller 41 determines that the current time is time t7 (Yes in S42), light emission controller 41 starts the boost control (S26). As illustrated in FIG. 16, at time t7, light emission controller 41 starts the boost control for causing light emitter 50 to emit light at more steeply increasing luminance than in the predetermined brightening pattern (a broken line in (b) of FIG. 16).

As described above, light emission controller 41 (illumination system 100*b*) starts the boost control in the boundary state between the REM sleep state and the hypnagogic state, the boundary state being a state in which brain activity is relatively mild and a sleep state is relatively shallow. With this, it is possible to allow the user to wake up comfortably.

It should be noted that illumination system 100*b* may include a sound emitter such as a speaker, and may allow the user to wake up comfortably, by coordinating light emitted by light emitter 50 and sound (audio or music) emitted by the sound emitter. Illumination system 100*b* may include a display (e.g., a display panel) which displays an image or a projector (e.g., a projector apparatus) which projects an image, and may allow the user to wake up comfortably, by coordinating light emitted by light emitter 50 and the image displayed or projected.

[Second Example of Wake-up Control According to Embodiment 3]

Figure 17:
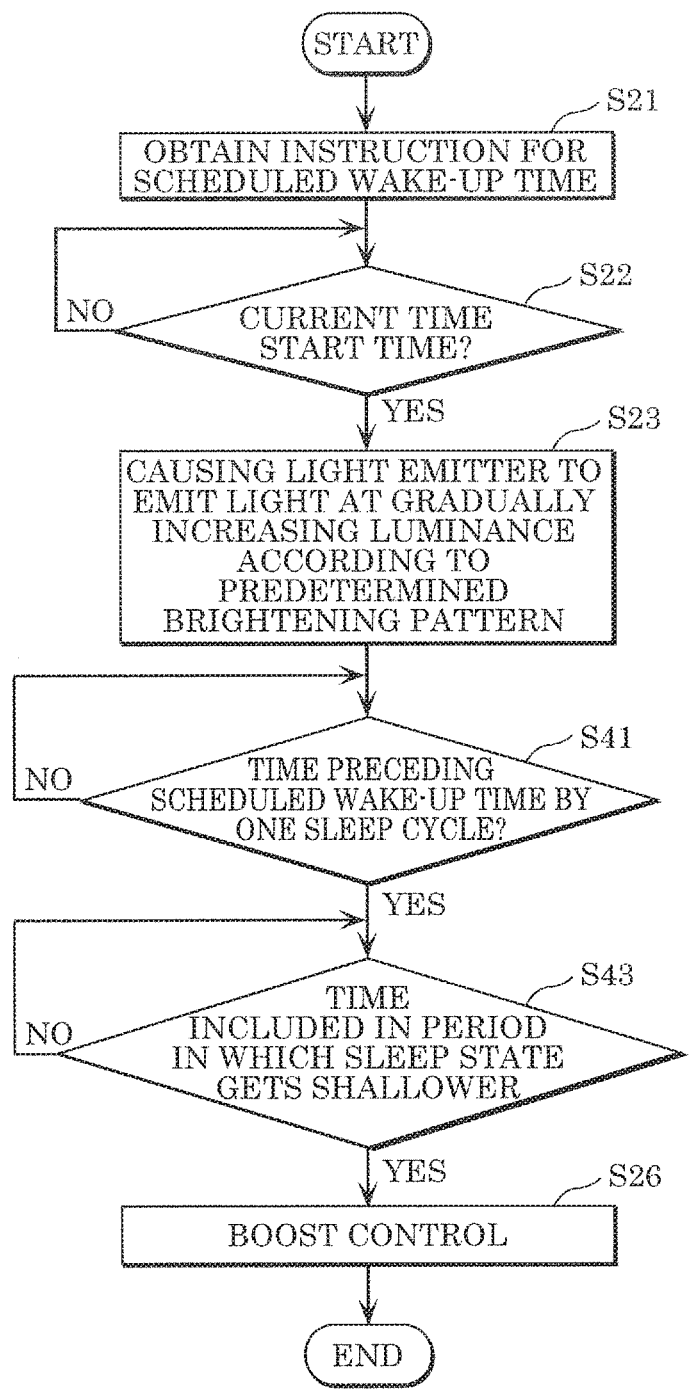
FIG. 17 is a flow chart for a second example of the wake-up control according to Embodiment 3.
Figure 18:
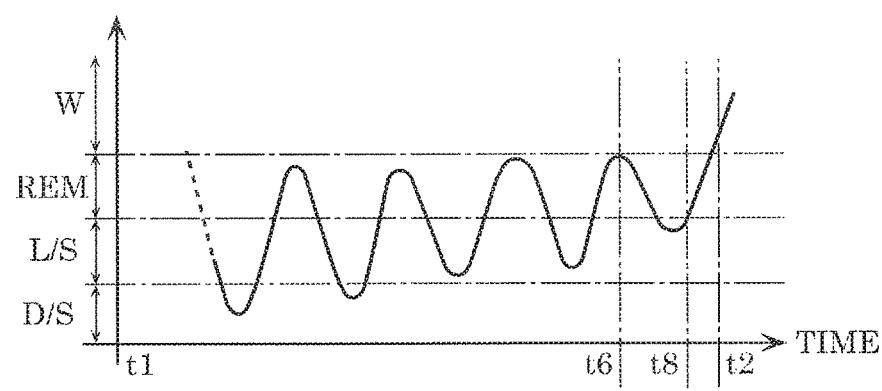
FIG. 18 is a graph illustrating a sleep state and luminance of the light emitter in the second example of the wake-up control according to Embodiment 3.
Figure 18:
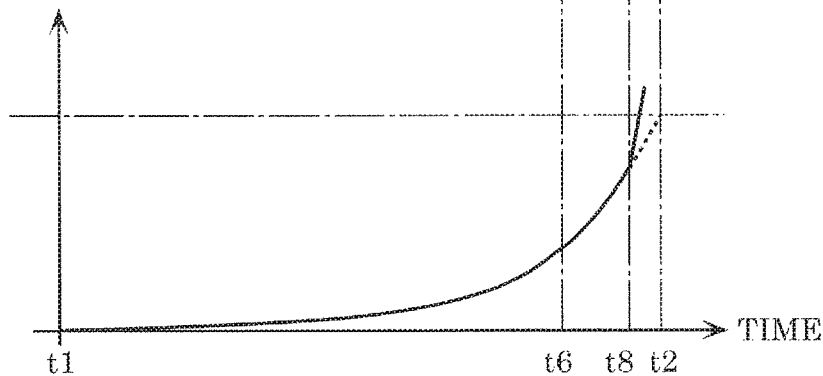

Next, the following describes a second example of the wake-up control according to Embodiment 3. FIG. 17 is a flow chart for the second example of the wake-up control according to Embodiment 3. FIG. 18 is a graph illustrating a sleep state ((a) of FIG. 18) and luminance of light emitter 50 ((b) of FIG. 18) in the second example of the wake-up control according to Embodiment 3. The following description of the second example of the wake-up control according to Embodiment 3 will be centered on differences from the first example of the wake-up control according to Embodiment 3.

In the second example of the wake-up control according to Embodiment 3, when light emission controller 41 determines that the current time is time t6 preceding scheduled wake-up time t2 by one sleep cycle (Yes in S41), light emission controller 41 determines whether the current time is time t8 included in a period in which a sleep state of the user gets shallower (S43). This determination is continuously made until, for example, the current time is start time t8 (No in S43). It should be noted that time t8 is a time included in one sleep cycle ending at scheduled wake-up time t2.

When the shallower the sleep state gets, the greater a value is as illustrated in FIG. 18, the period in which the sleep state of the user is a period in which the sleep state monotonously increases. Although such a period in which the sleep state gets shallower is identified based on the sleep state of the user (an actual value) determined by determiner 45 after time t6, the period may be identified based on prediction of a sleep state made by predictor 46.

When light emission controller 41 determines that the current time is time t8 (Yes in S43), light emission controller 41 starts the boost control (S26). As illustrated in FIG. 18, at time t8, light emission controller 41 starts the boost control for causing light emitter 50 to emit light at more steeply increasing luminance than in the predetermined brightening pattern (a broken line in (b) of FIG. 18).

As described above, light emission controller 41 (illumination system 100*b*) allows the user to wake up comfortably, by starting the boost control in the period in which the sleep state of the user gets shallower.

[Advantageous Effects Etc. of Embodiment 3]

As described above, light emission control device 40*b* of illumination system 100*b* according to Embodiment 3 further includes predictor 46 which predicts a sleep cycle of the user. Light emission controller 41 starts the boost control at a time included in one sleep cycle which is predicted by predictor 46 and ends at scheduled wake-up time t2 of the user.

With this, light emission controller 41 (illumination system 100*b*) allows the user to wake up comfortably because light emission controller 41 starts the boost control at a time preceding scheduled wake-up time t2 by one sleep cycle.

Moreover, light emission controller 41 may start the boost control at a time which is included in the one sleep cycle predicted by predictor 46 and at which the user is determined to be in a boundary state between a REM sleep state and a sleep state deeper than the REM sleep state.

With this, light emission controller 41 (illumination system 100*b*) allows the user to wake up comfortably because light emission controller 41 starts the boost control in the boundary state between the REM sleep state and the hypnagogic state, the boundary state being a state in which brain activity is relatively mild and a sleep state is relatively shallow.

Moreover, light emission controller 41 may start the boost control at a time which is included in the one sleep cycle predicted by predictor 46 and which is determined to be included in a period in which the sleep state gets shallower in the one sleep cycle.

With this, light emission controller 41 (illumination system 100*b*) allows the user to wake up comfortably because light emission controller 41 starts the boost control in the period in which the sleep state of the user gets shallower.

(Other Embodiments)

The embodiments have been described above, but the present disclosure is not limited to the aforementioned embodiments.

For example, a process performed by one structural component may be performed by another structural component in the aforementioned embodiments. Moreover, processes performed by respective structural components may be collectively performed by one structural component. For example, although the determination of the sleep state is performed by the determiner and the prediction of the sleep cycle is performed by the predictor in the aforementioned embodiments, the determination of the sleep state and the prediction of the sleep cycle may be performed by one structural component.

Moreover, the arrangement of the structural components included in the luminaire may be changed appropriately. For example, the communicator included in the luminaire may be included in the light emission control device, and structural components such as the clock, the determiner, the storage, and the dimming circuit included in the light emission control device may be disposed outside of the light emission control device. The light emission control device may include at least the light emission controller.

For example, an LED (or an LED element) is given as an example of a light-emitting element used in the light emitter in the aforementioned embodiments. However, another solid-state light-emitting element such as a semiconductor light-emitting element such as a semiconductor laser or an electroluminescent (EL) element such as an organic EL element or an inorganic EL element may be used as the light emitter.

Moreover, general or specific aspects of the present disclosure may be realized as a system, device, method, integrated circuit, computer program, non-transitory computer-readable medium such as a CD-ROM, or any given combination thereof. For example, one aspect of the present disclosure may be realized as an illumination system according to the aforementioned embodiments. One aspect of the present disclosure may be realized as a method for controlling a light emitter performed by a light emission control device, as a program causing a computer to execute the method, or as a non-transitory recording medium onto which such a program is stored.

While the foregoing has described one or more embodiments and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. A light emission control device comprising:
a light emission controller which controls a light emitter and performs normal control and wake-up control, the normal control being control for causing the light emitter to emit light having a color temperature and luminance according to an instruction of a user, the wake-up control being control for causing the light emitter to emit light at increasing luminance over time to wake up the user who is sleeping,
wherein maximum luminance of light emitted by the light emitter in the wake-up control is greater than maximum luminance of light emitted by the light emitter in the normal control,
the light emitter includes a first light source and a second light source which emits light having a color temperature higher than a color temperature of light emitted by the first light source,
the maximum luminance of the light emitted by the light emitter in the normal control is equivalent to maximum luminance of light which the user is allowed to cause the first light source to emit, and
in the wake-up control, the light emission controller causes the light emitter to emit light having luminance greater than the maximum luminance of the light emitted by the light emitter in the normal control, by causing, out of the first light source and the second light source, the second light source to emit light.

2. The light emission control device according to claim 1, wherein in the wake-up control, the light emission controller causes the light emitter to emit light having luminance greater than the maximum luminance of the light emitted by the light emitter in the normal control, by causing the second light source to emit brighter light than the first light source does.

3. The light emission control device according to claim 1, wherein the light emitted by the first light source has a color temperature of at most 3000 K, and
the light emitted by the second light source has a color temperature of at least 5000 K.

4. The light emission control device according to claim 1, wherein in the wake-up control, when the light emission controller causes the light emitter to emit light at increasing luminance over time according to a predetermined brightening pattern, the light emission controller further performs boost control, the boost control being control for causing the light emitter to emit light at more steeply increasing luminance than in the predetermined brightening pattern.

5. The light emission control device according to claim 4, further comprising:
a processor which determines a sleep state of the user,
wherein the light emission controller starts the boost control at a time when the user is determined to be in a state other than a rapid eye movement (REM) sleep state.

6. A light emission control device comprising:
a light emission controller which controls a light emitter and performs normal control and wake-up control, the normal control being control for causing the light emitter to emit light having a color temperature and luminance according to an instruction of a user, the wake-up control being control for causing the light emitter to emit light at increasing luminance over time to wake up the user who is sleeping,
wherein maximum luminance of light emitted by the light emitter in the wake-up control is greater than maximum luminance of light emitted by the light emitter in the normal control,
in the wake-up control, when the light emission controller causes the light emitter to emit light at increasing luminance over time according to a predetermined brightening pattern, the light emission controller further performs boost control, the boost control being control for causing the light emitter to emit light at more steeply increasing luminance than in the predetermined brightening pattern, and
the light emission controller starts the boost control at a time when the user is determined to be in any one of a wakeful state, a hypnagogic state, and a light sleep state,
the light emitter includes a first light source and a second light source which emits light having a color temperature higher than a color temperature of light emitted by the first light source,
the maximum luminance of the light emitted by the light emitter in the normal control is equivalent to maximum luminance of light which the user is allowed to cause the first light source to emit, and
in the wake-up control, the light emission controller causes the light emitter to emit light having luminance greater than the maximum luminance of the light emitted by the light emitter in the normal control, by causing, out of the first light source and the second light source, the second light source to emit light.

7. The light emission control device according to claim 4, further comprising:
a processor which predicts a sleep cycle of the user,
wherein the light emission controller starts the boost control at a time included in one sleep cycle which is predicted by the processor and ends at a scheduled wake-up time of the user.

8. The light emission control device according to claim 7, wherein the processor further determines a sleep state of the user,
wherein the light emission controller starts the boost control at a time which is included in the one sleep cycle predicted by the processor and at which the user is determined to be in a boundary state between a rapid eye movement (REM) sleep state and a sleep state deeper than the REM sleep state.

9. The light emission control device according to claim 7, wherein the processor further determines a sleep state of the user,
wherein the light emission controller starts the boost control at a time which is included in the one sleep cycle predicted by the processor and which is determined to be included in a period in which the sleep state gets shallower in the one sleep cycle.

10. An electronic device comprising:
the light emission control device according to claim 1; and
a case which houses the light emission control device.

11. The electronic device according to claim 10, the electronic device being a luminaire further including the light emitter.

12. A method for controlling a light emitter, the method comprising:
performing normal control and wake-up control, the normal control being control for causing the light emitter to emit light having a color temperature and luminance according to an instruction of a user, the wake-up control being control for causing the light emitter to emit light at increasing luminance over time to wake up the user who is sleeping,
wherein maximum luminance of light emitted by the light emitter in the wake-up control is greater than maximum luminance of light emitted by the light emitter in the normal control,
the light emitter includes a first light source and a second light source which emits light having a color temperature higher than a color temperature of light emitted by the first light source, and
the maximum luminance of the light emitted by the light emitter in the normal control is equivalent to maximum luminance of light which the user is allowed to cause the first light source to emit, and
in the wake-up control, light emitted by the light emitter has luminance greater than the maximum luminance of the light emitted by the light emitter in the normal control, by causing, out of the first light source and the second light source, the second light source to emit light.

13. A non-transitory computer-readable recording medium for use in a computer, the recording medium having a computer program recorded thereon for causing the computer to execute the method according to claim 12.

14. The light emission control device according to claim 1,
wherein in the normal control, maximum luminance of light having any color temperature emitted by the light emitter is equivalent to maximum luminance of light which the user is allowed to cause the first light source to emit.

* * * * *